United States Patent

Nappholz et al.

[11] Patent Number: 5,817,136
[45] Date of Patent: Oct. 6, 1998

[54] RATE-RESPONSIVE PACEMAKER WITH MINUTE VOLUME DETERMINATION AND EMI PROTECTION

[75] Inventors: Tibor A. Nappholz, Englewood; Saul E. Greenhut, Aurora, both of Colo.; Chih-ming James Chiang, Chandler, Ariz.

[73] Assignee: Pacesetter, Inc., Sylmar, Calif.

[21] Appl. No.: 850,529

[22] Filed: May 2, 1997

[51] Int. Cl.$^6$ ................................ A61N 1/365
[52] U.S. Cl. ................ 607/17; 607/20; 607/28
[58] Field of Search .................. 607/9, 17–20, 607/27, 28

[56] References Cited

U.S. PATENT DOCUMENTS

| | | |
|---|---|---|
| 4,901,725 | 2/1990 | Nappholz et al. . |
| 5,441,523 | 8/1995 | Nappholz . |
| 5,487,753 | 1/1996 | MacCarter et al. . |
| 5,562,711 | 10/1996 | Yerich et al. . |
| 5,562,712 | 10/1996 | Steinhaus et al. . |
| 5,591,214 | 1/1997 | Lu .................................... 607/9 |
| 5,626,622 | 5/1997 | Cooper . |
| 5,647,379 | 7/1997 | Meltzer . |
| 5,697,958 | 12/1997 | Paul et al. . |
| 5,702,425 | 12/1997 | Wickham . |

*Primary Examiner*—William E. Kamm
*Assistant Examiner*—Carl H. Layno
*Attorney, Agent, or Firm*—Gootlieb, Rackman & Reisman, P.C.

[57] ABSTRACT

A rate responsive pacemaker includes a noise sensor for sensing noise on the leads. If noise is detected, the pacemaker switches to a mode wherein a metabolic demand parameter is ignored. The noise is preferably detected by using test signals which are also used to measure the metabolic demand parameter.

14 Claims, 8 Drawing Sheets

5,817,136

RATE-RESPONSIVE PACEMAKER WITH MINUTE VOLUME DETERMINATION AND EMI PROTECTION

RELATED APPLICATIONS

| | | |
|---|---|---|
| RATE-RESPONSIVE PACEMAKER WITH RAPID MINUTE VOLUME DETERMINATION | 08/850,557 | 5/2/97 |
| RATE-RESPONSIVE PACEMAKER WITH NOISE-REJECTING MINUTE VOLUME DETERMINATION | 08/848,968 | 5/2/97 |
| RATE-RESPONSIVE PACEMAKER WITH EXERCISE RECOVERY USING MINUTE VOLUME DETERMINATION | 08/850,692 | 5/2/97 |

BACKGROUND OF THE INVENTION

1. Field of the Invention

This invention relates to rate-responsive pacemakers and, more particularly, to pacemakers that employ a minute volume metabolic demand sensor as a metabolic rate indication, said sensor operating fast to thereby insure that the pacemaker reacts accurately to changes in the level of activity while ensuring immunity to radio frequency electromagnetic interference and erroneous baseline setting.

2. Description of the Prior Art

Many attempts have been made to control the heart rate of a pacemaker patient so that it will duplicate the intrinsic heart rate of a healthy person both when the patient is at rest and when the patient is involved in various levels of exercise. Metabolic demand related parameters heretofore proposed for controlling the pacing rate include the QT interval, respiration rate, venous oxygen saturation, stroke volume, venous blood temperature, and minute volume or ventilation, among others. (The terms minute ventilation and minute volume are used interchangeably). In addition, the use of mechanical and electrical sensors which detect patient motion have also been explored in such attempts at achieving improved rate-responsiveness. Of the various parameters available, it has been found that pacemakers using minute volume as a parameter for controlling pacing rate are particularly advantageous.

However, a problem with these types of pacers has been that the minute ventilation sensors are vulnerable to high frequency electromagnetic interference (EMI) which adds noise to the thoracic impedance signal and which may cause pacing at or near the maximum rate, causing discomfort and lack of well-being to patients. The sensor is potentially vulnerable in a hospital setting, where EMI (such as from electrocautery) is particularly prevalent.

A further problem is that the MV sensor requires initial assessment of a baseline minute ventilation value. If the initial adaptation occurs prior to implantation or while the pacemaker has not been implanted properly within the patient, then the sensor indicated rate might be inappropriate and may cause problems.

OBJECTIVES AND SUMMARY OF THE INVENTION

In view of the above mentioned disadvantages of the prior art, it is an objective of the present invention to provide a pacemaker which dynamically responds to the instantaneous physical level of activity of a patient and adjusts its pulse rate accordingly.

Another objective is to ensure shutdown of rate responsive function of a pacemaker before its implantation.

Another objective is to provide a pacemaker which automatically ensures that the pacer and lead connection has been properly implanted before allowing the sensor to initiate operation.

Yet another objective of the invention is to provide a pacemaker which would shield the sensor from EMI to prevent inappropriate therapy.

Other objectives and advantages of the invention shall become apparent from the following description. Briefly, a pacemaker constructed in accordance with this invention includes sensing means for sensing a metabolic demand parameter of the patient indicative of his or her instantaneous physical activity. Preferably, the metabolic demand parameter is minute volume which can be determined, for example, from impedance measurements. Minute volume has been found to be an accurate representation of the physical activity and the corresponding blood flow and oxygen demand of a patient. A safeguard circuit is provided which disables the sensor function if the pacer has not yet been properly implanted in the patient with correct lead attachment. A further circuit is provided to filter the raw impedance signal obtained and reject the signal if EMI interference is present. If the signal passes through the safeguard circuitry, then the parameter is converted into a corresponding metabolic indicated rate (MIR), which rate may be used to define the interval between the pacer pulses. The mapping of minute volume to metabolic indicated rate (MIR), preferably, uses a preselected curve which may be, for example, an exponential curve, or other monotonic curves. The resulting rate is then used to calculate a optimal paced pulse interval.

DETAILED DESCRIPTION OF THE INVENTION

Figure 1:
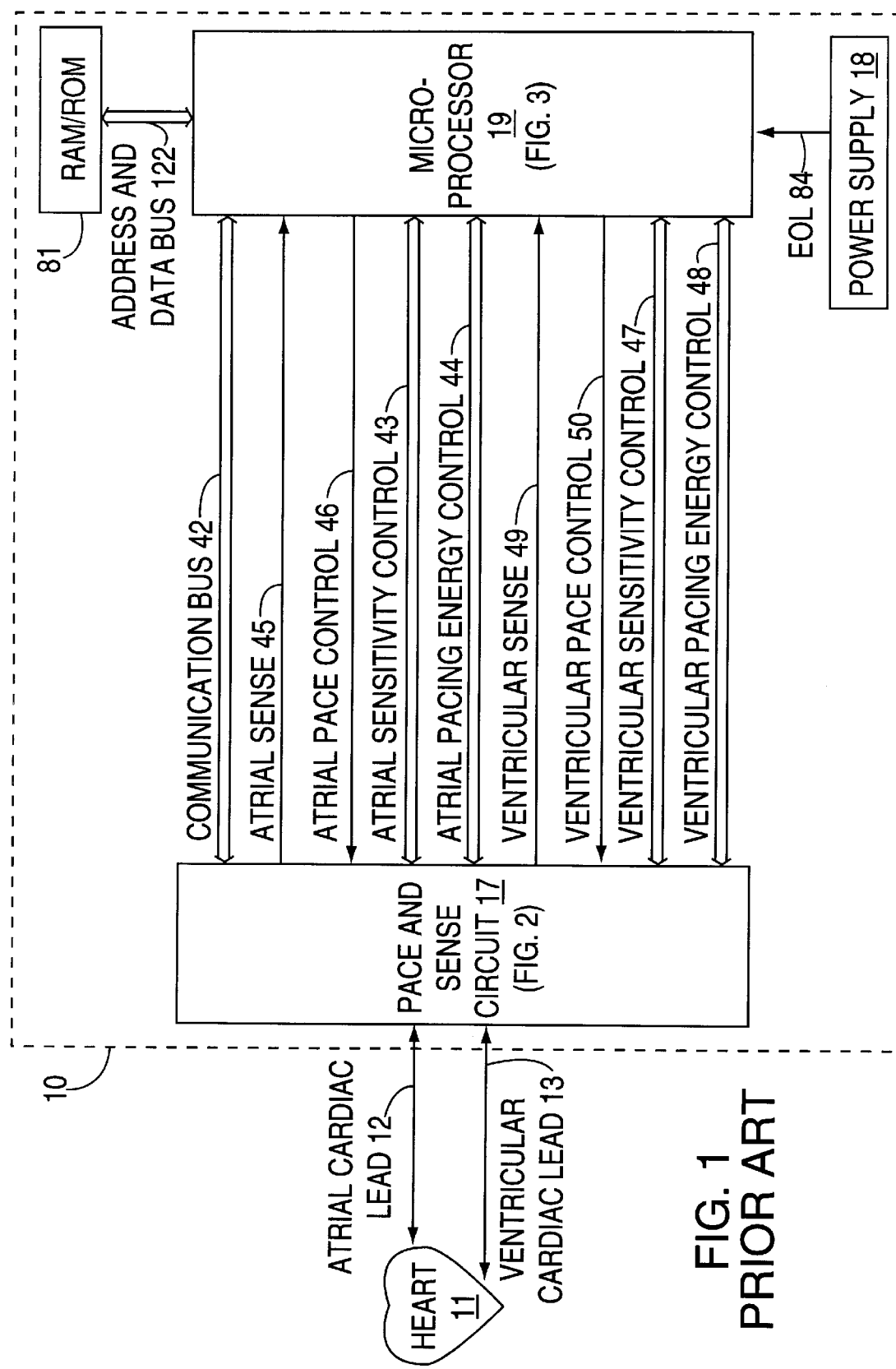
FIG. 1 shows a block diagram of a pacemaker constructed in accordance with this invention.

Details of a pacemaker in accordance with the present invention are shown in FIGS. 1–6. FIG. 1 shows a block diagram of the pacemaker. The pacemaker 10 is designed to be implanted in a patient and is connected by leads 12 and 13 to a patient's heart 11 for sensing and pacing the heart 11 as described for example in U.S. Pat. No. 5,441,523 by T. Nappholz, entitled FORCED ATRIOVENTRICULAR SYNCHRONY DUAL CHAMBER PACEMAKER, and incorporated herein by reference. Briefly, the atrial cardiac lead 12 extends into the atrium of the heart 11 and the ventricular cardiac lead 13 extends into the ventricle of the heart 11. Leads 12 and 13 are used for both sensing electrical activity in the heart and for applying pacing pulses to the heart. The pacemaker 10 includes a pace and sense circuit 17 for the detection of analog signals from leads 12 and 13 and for the delivery of pacing pulses to the heart; a microprocessor 19 which, in response to numerous inputs received from the pace and sense circuit 17, performs operations to generate different control and data outputs to the pace and sense circuit 17; and a power supply 18 which provides a voltage supply to the pace and sense circuit 17 and the microprocessor 19 by electrical conductors (not shown). The microprocessor 19 is connected to a random access memory/read only memory unit 81 by an address and data bus 122. A low power signal line 84 is used to provide to the microprocessor 19 a logic signal indicative of a low energy level of the power supply 18. The microprocessor 19 and the pace and sense circuit 17 are connected to each other by a number of data and control lines including a communication bus 42, an atrial sense line 45, an atrial pacing control line 46, an atrial sensitivity control bus 43, an atrial pace energy control bus 44, a ventricular sense line 49, a ventricular pace control line 50, a ventricular sensitivity control bus 47, and a ventricular pacing energy control bus 48.

Figure 2:
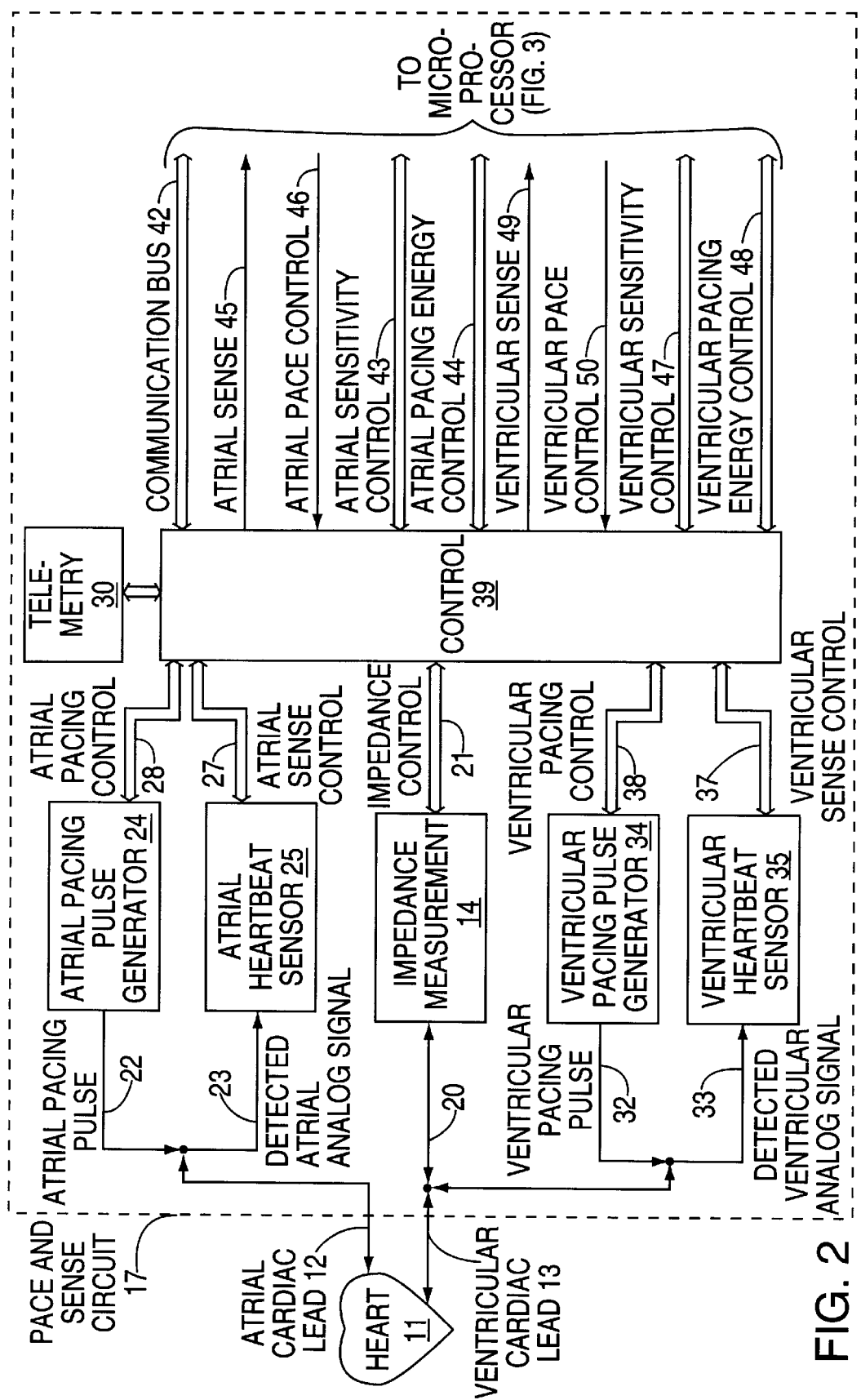
FIG. 2 shows a block diagram of the pace and sense circuit for the pacemaker of FIG. 1.

FIG. 2 shows details of the pace and sense circuit 17. The circuit 17 includes an atrial pacing pulse generator 24, a ventricular pacing pulse generator 34, an atrial heartbeat sensor 25, a ventricular heartbeat sensor 35, and a telemetry circuit 30. The preferred embodiment of the pace and sense circuit 17 also includes an impedance measurement circuit 14 for measuring a physiological parameter indicative of the patient's metabolic demand. The pace and sense circuit 17 also includes a control block 39 which is interfaced to the microprocessor 19.

In operation, the atrial and ventricular heartbeat sensor circuits 25 and 35 detect respective atrial and ventricular analog signals 23 and 33 from the heart 11 and convert the detected analog signals to digital signals. In addition, the heartbeat sensor circuits 25 and 35 receive an input atrial sense control signal on a control bus 27 and an input ventricular sense control signal on a control bus 37, respectively, from the control block 39. These control signals are used to set the sensitivity of the respective sensors.

The atrial pacing pulse generator circuit 24 receives from the control block 39, via an atrial pacing control bus 28, an atrial pace control signal and an atrial pacing energy control signal to generate an atrial pacing pulse 22 at appropriate times. Similarly, the ventricular pacing pulse generator circuit 34 receives from the control block 39, via a ventricular pacing control bus 38, a ventricular pace control signal and a ventricular pacing energy control signal to generate a ventricular pacing pulse 32. The atrial and ventricular pace control signal determine the respective timing of atrial and ventricular pacing that take place, while the atrial and ventricular pacing energy control inputs determine the respective magnitudes of the pulse energies.

The pacemaker 10 makes an impedance measurement when the microprocessor 19 sends a signal on the impedance control bus 21 to activate the impedance measurement circuit 14. The impedance measurement circuit 14 then applies a current to the ventricular cardiac lead 13 via lead 20 and measures a voltage resulting from the applied current, as discussed in more detail below. These current and voltage signals define an impedance characteristic of the patient's metabolic demand, and more particularly, of the instantaneous minute volume. This instantaneous minute volume is then filtered and further modified by subtracting from it a long term average value, as discussed below. The resulting parameter is the minute volume parameter.

The telemetry circuit 30 provides a bidirectional link between the control block 39 of the pace and sense circuit 17 and an external device such as a programmer. It allows data such as the operating parameters to be read from or altered in the implanted pacemaker. An exemplary programmer is the Model 9600 Network Programmer manufactured by Telectronics of Englewood, Colo. U.S.A.

Figure 3:
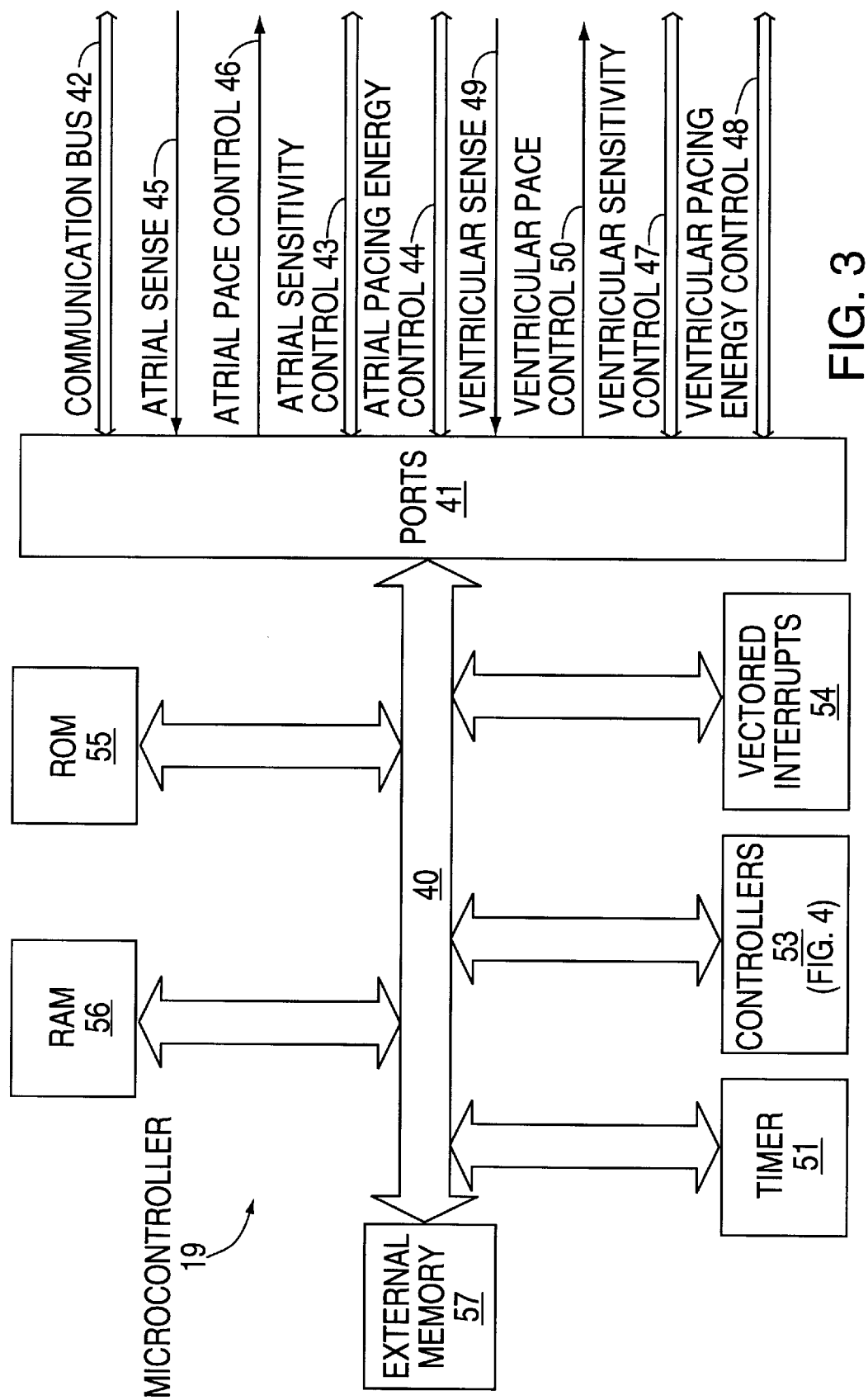
FIG. 3 shows a block diagram of a microprocessor for the pacemaker of FIG. 2.

FIG. 3 shows the microprocessor 19 having a timer circuit 51 for generating several timing signals on its output ports, a controller 53, a vectored interrupts circuit 54, a ROM 55, a RAM 56, an external memory 57 and an interface port 41. Signals between these elements are exchanged via an internal communications bus 40. Timer circuits generate various timing signals at its output ports. The RAM 56 acts as a scratchpad and active memory during execution of the programs stored in the ROM 55 and used by the microprocessor 19. ROM 55 is used to store programs including system supervisory programs, detection algorithms for detecting and confirming arrhythmias, and programming for determining the rate of the pacer, as well as storage programs for storing, in external memory 57, data such as that concerning the functioning of the pulse generator 10 and the electrogram provided by the ventricular cardiac lead 13. The timer circuit 51, and its associated control software, implements some timing functions required by the microprocessor 19 without resorting entirely to software, thus reducing computational loads on, and power dissipation by, the controller 53.

Signals received from the telemetry circuit 30 permit an external programmer (not shown) to change the operating parameters of the pace and sense circuit 17 by supplying appropriate signals to the control block 39. The communication bus 42 serves to provide signals indicative of such control to the microprocessor 19.

The microprocessor 19 through its port 41 receives status and/or control inputs from the pace and sense circuit 17, including the sense signals on the sense lines 45 and 49 previously described. Using controller 53, it performs various operations, including arrhythmia detection, and produces outputs, such as the atrial pace control on the line 46 and the ventricular pace control on the line 50, which determine the type of pacing that is to take place. Other control outputs generated by the microprocessor 19 include the atrial and ventricular pacing energy controls on the buses 44 and 48, respectively, which determine the magnitude of the pulse energy, and the atrial and ventricular sensitivity controls on the buses 43 and 47, respectively, which set the sensitivities of the sensing circuits. The rate of the atrial and/or ventricular pacing is adjusted by controller 53 as set forth below.

The pacemaker 10 of the present invention will function properly using any metabolic indicator rate system, so long as that system is able to reliably relate the sensed parameter to an appropriate matching of metabolic demand with the paced rate. However, the preferred embodiment of the invention employs the impedance measurement circuit 14, shown in FIG. 5, which measures the cardiac impedance to determine the respiratory minute volume as described generally in U.S. Pat. No. 4,901,725 to T. A. Nappholz, et al., issued Feb. 20, 1990 for "Minute Volume Rate-Responsive Pacemaker", incorporated herein by reference.

Figure 4:
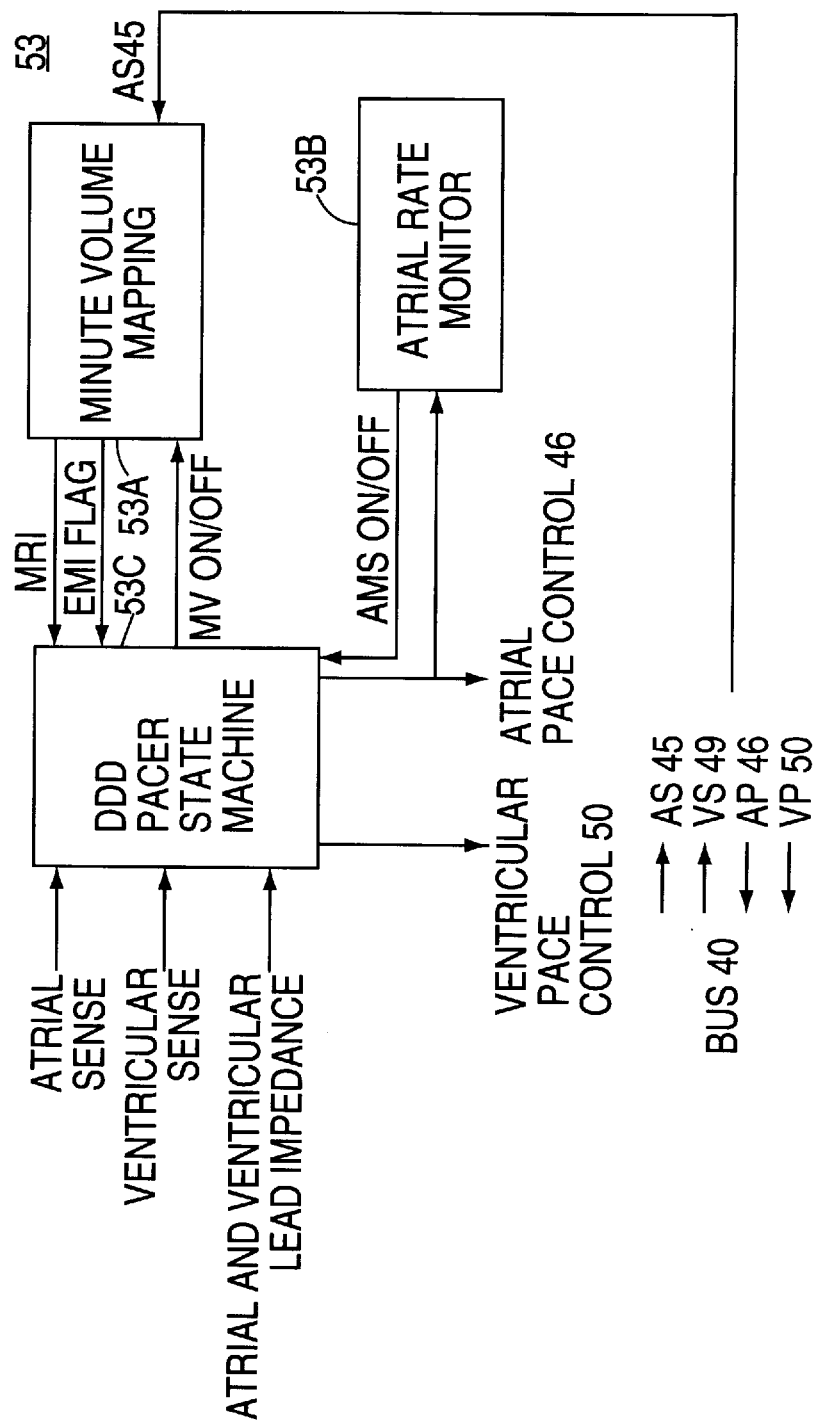
FIG. 4 shows details of the controller for the microprocessor of FIG. 3 with EMI flag generated by FIG. 6.

FIG. 4 shows the block diagram of the controller 53 of FIG. 3. The controller 53 includes a pacer 53C, which is preferably a state machine, a minute volume processor 53A and an atrial rate monitor 53B. The minute volume processor 53A uses the data supplied via the internal bus 40 and the communication bus 42 from the impedance measurement block 14 to relate the minute volume indicated by the impedance measurement to the Metabolic Rate Interval (MRI). This interval is then used by the pacer 53C to determine the length of each interval in the timing cycle. While the pacemaker 10 is preferably operating in a DDD mode, it should be understood that it can operate in other modes as well. The atrial rate monitor 53B generates an Automatic Mode Switching (AMS) signal upon detection of a non-physiological atrial rate and rhythm. This AMS signal automatically switches the pacemaker 10 to a non-atrial-tracking mode. When a physiological atrial rate resumes, the AMS signal is deactivated and the pacemaker returns to an atrial tracking mode.

The DDD Pacer State Machine circuit 53 also receives lead impedance signals from both the atrium and ventricle as input. If the lead impedance from the particular chamber(s) where minute ventilation is measured from is extremely high (>2000Ω), this would indicate potential problems with the particular lead such as lead conductor fracture and/or improper connection and/or improper implantation and/or no implantation. Under these circumstances, the Minute Volume Mapping 53A is turned off, as indicated by the On/Off line input to Minute Volume Mapping 53A. This includes inactivating the updating of short and long-term averages of MV.

Figure 5:
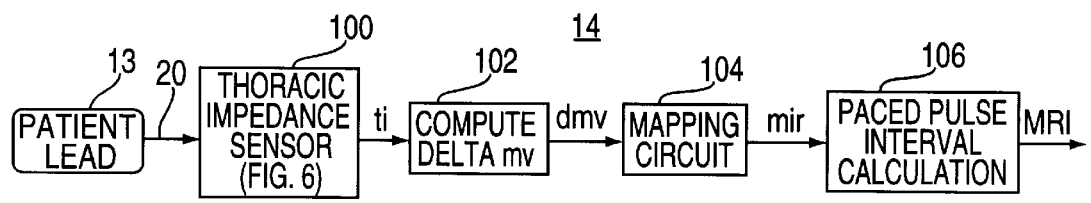
FIG. 5 shows details of the minute volume processor for the controller of FIG. 4.

Referring now to FIG. 5, the impedance measurement circuit 14 includes a thoracic impedance sensor 100 which is coupled by connection 20 to one of the patient's leads, such as lead 13. The sensor 100 generates a time-dependent signal ti indicative of the sensed thoracic impedance of the patient. The signal is fed to a delta mv generator 102 which converts this ti signal into a corresponding dmv signal. Several implementations of this delta minute ventilation (dmv) generator 102 can be found in U.S. Pat. No. 5,441,521 and in the above-named application entitled RATE-RESPONSIVE PACEMAKER WITH NOISE-REJECTING MINUTE VOLUME DETERMINATION both incorporated herein by reference. The signal dmv is fed to a mapping circuit 104 which uses a conformal mapping (discussed in more detail below) to generate a corresponding metabolic indicated rate MIR. Then it is outputted through the paced pulse interval calculation and MRI generated.

Figure 6:
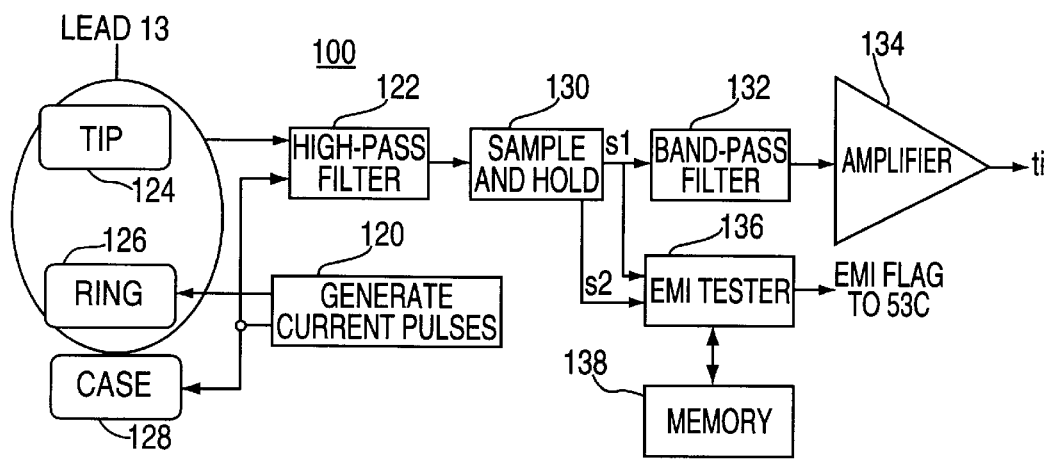
FIG. 6 shows a block diagram for the circuit used to determine thoracic impedance and the flag signal needed to ensure proper MV activation in FIG. 4.

Referring now to FIG. 6, thoracic impedance sensor 100 includes a current generator 120 and a high pass filter 122 coupled to one of the patient leads, such as lead 13. (It should be clear that other leads may be used as well for determining the mv parameter as described for example in U.S. Pat. No. 5,562,712). The lead 13 includes a tip electrode 124 and a ring electrode 126. As known in the art, at predetermined times, the current generator 120 applies current pulses between the ring electrode 126 and pacemaker case 128, and the corresponding voltage is sensed between the tip electrode 124 and case 128.

Typically, each current pulse has a pulse width of about 7.5 μsec, at repetition rate of about 18 pulses per second and an amplitude of about 1 mA. This pulse repetition rate is chosen at well above twice the Nyquist sampling rate for the highest expected intrinsic heart beats, and is chosen so that it can be easily differentiable from noise induced by a power line at 50 or 60 Hz.

Figure 7A:
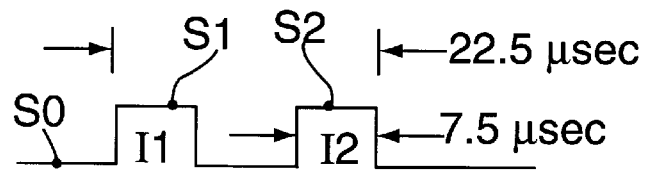
FIG. 7A shows a first example of current pulses for detecting EMI interference.
Figure 7B:
FIG. 7B shows the signal sensed from the heart responsive to the test pulses of FIG. 7A when contaminated with EMI.
Figure 7C:
FIG. 7C shows the signal sensed from the heart without EMI.

In order to detect EMI in the present invention, instead of a single current pulse, pulse generator generates two 7.5 μsec pulses I1 and I2 separated by 7.5 μsec interval as shown in FIG. 7A. In the presence of EMI, the voltage sensed responsive to the two current pulses of FIG. 7A is shown in FIG. 7B. FIG. 7C shows the voltage response without EMI. Both of the responses of FIGS. 7B and 7C are shown as being sampled at S1 and S2, toward the end of each of the current pulses I1 and I2.

FIGS. 7B and 7C show that there is a remarkable difference between the samples at S1, S2 in the presence of EMI while there is substantially no difference between the samples taken at S1 and S2 in the absence of EMI.

The high pass filter 122 is selected to accept the 7.5 μsec pulses and exclude all noise signals. After filtering, the voltage signal is sampled by a sample and hold (S/H) circuit 130. Preferably the S/H circuit takes a sample (at S0) before the start of the test pulses from generator 120 (to enhance the effectiveness of the filter 122) as well as toward the end of the pulse duration (i.e., at S1 and S2). Samples S1 and S2 are also fed to an EMI detection current 136.

Figure 8:
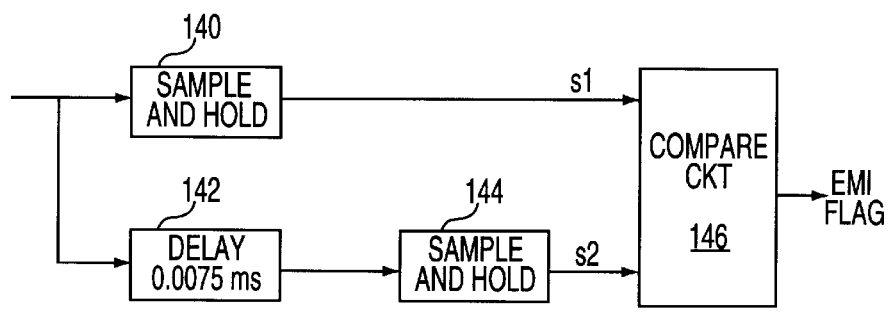
FIG. 8 shows details of the sample and hold circuit.

As shown in FIG. 8, circuit 136 contains a delay 142 (of 15 μsecs) a second S/H circuit 144 and a comparator 136.

The output s1 of circuit 130 is passed through a band pass filter 132 which selects the signals in the range of normal respiration rate, which is typically in the range of 5–60 cycles/minute.

The output of the BPF 132 is amplified by amplifier 134 to thereby generate the thoracic impedance signal ti. The amplifier raises the signal ti to a level sufficient so that it can be sensed and processed by the delta minute volume generator 102.

Figure 9:
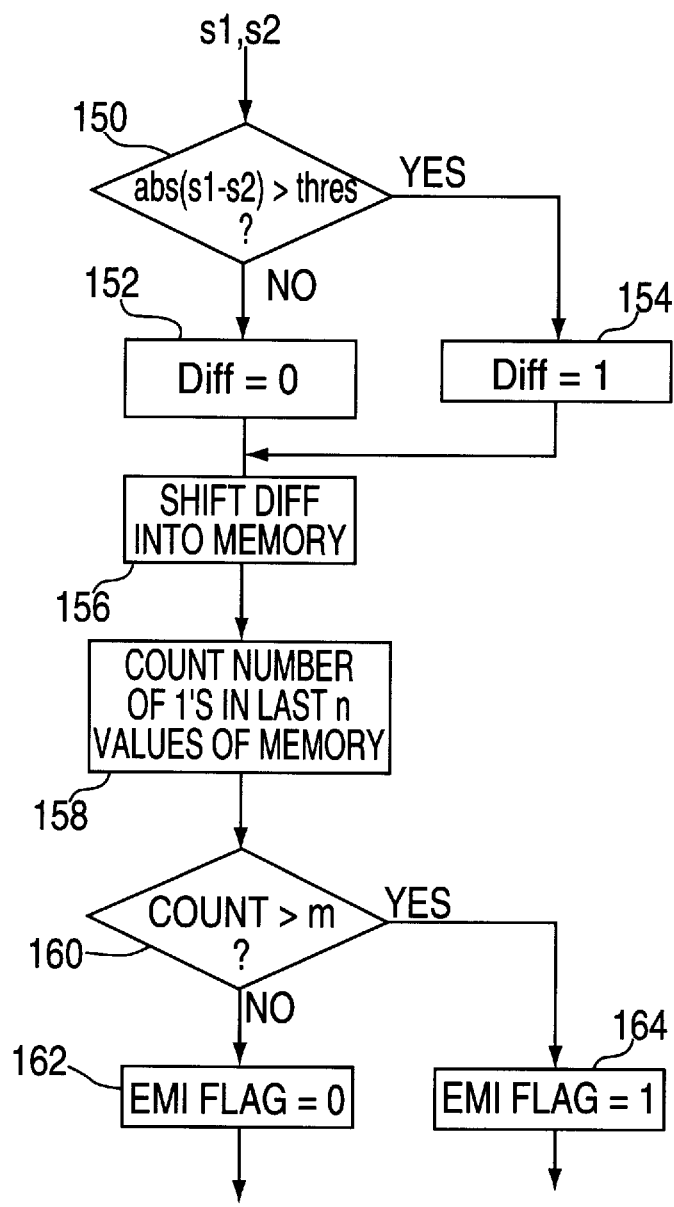
FIG. 9 shows the flowchart for detecting EMI interference.

Referring now to FIG. 9, the EMI detection circuit 136 (FIG. 8) performs the following functions. In step 150 the absolute difference between S1 and S2 is compared to a preset threshold value (thres). If this absolute value is greater than thres, then in step 154 the parameter diff is set to '1'. Otherwise, diff is set to '0'. (Step 152). The value of diff is stored in step 156.

In Step 158, number of 1's of the last n values (e.g. 10) in the memory 138 (FIG. 6) are counted and set to variable count. If count is greater than the threshold m (Step 160), then the EMI flag is activated (Step 164) and sent to the DDD Pacer State Machine 53C in FIG. 4. Otherwise, the EMI flag is inactive (162). The value of m may be for example 7.

If the EMI Flag=0, then the DDD Pacer State Machine 53C would function as it normally does under rate responsive mode. However, if the EMI Flag=1, then the DDD Pacer State Machine 53C ignores input MRI from Minute Volume Mapping 53A and paces at the indicated rate at a specified time (e.g. 3 sec.) before the EMI Flag was activated. This continues until the EMI Flag is deactivated.

Figure 7D:
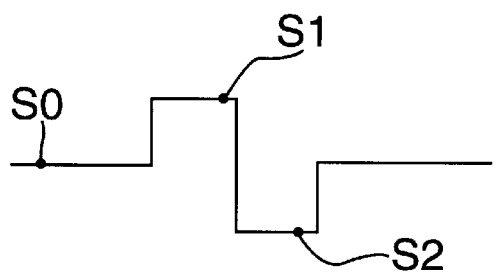
FIG. 7D shows a bipolar test signal applied to the heart.
Figure 7E:
FIG. 7E shows the response sensed to the test signal of FIG. 7D.

Instead of two (or more) test pulses of the same phase, multiphase current pulses may also be used. For instance, in FIG. 7D a bipolar current test pulse is used formed of two symmetrical pulse sections. The responsive voltage signal is sensed at S0, S1 and S2. Once again, in the presence of EMI, the samples at S1 and S2 have completely different amplitudes.

Returning to FIG. 5, the delta mv calculation circuit 102 calculates an instantaneous minute volume (dmv) every 1.5 seconds, with also possibly tidal volume (tv) and respiration rate (rr) generated as outputs, dependent upon the implementation. Details of the implementation may be found in U.S. Pat. No. 4,901,725 and the applications referenced above. This parameter dmv outputted from the delta mv generator 102 must be converted into a metabolic indicated rate (MIR) parameter. This mapping is converted in Circuit 104. Schemes for performing this function are well known in the art. One such scheme is disclosed in copending application Ser. No. 08/641,223 filed Apr. 30, 1996 and its continuation, application Ser. No. 08/823,077 filed Mar. 24, 1997, entitled RATE RESPONSIVE PACEMAKER WITH AUTOMATIC RATE RESPONSE FACTOR SELECTION incorporated herein by reference. As disclosed in this reference, a curvilinear mapping between minute ventilation and MIR is preferable because it can be modeled after physiological data on a wide range of normal subjects.

Figure 10:
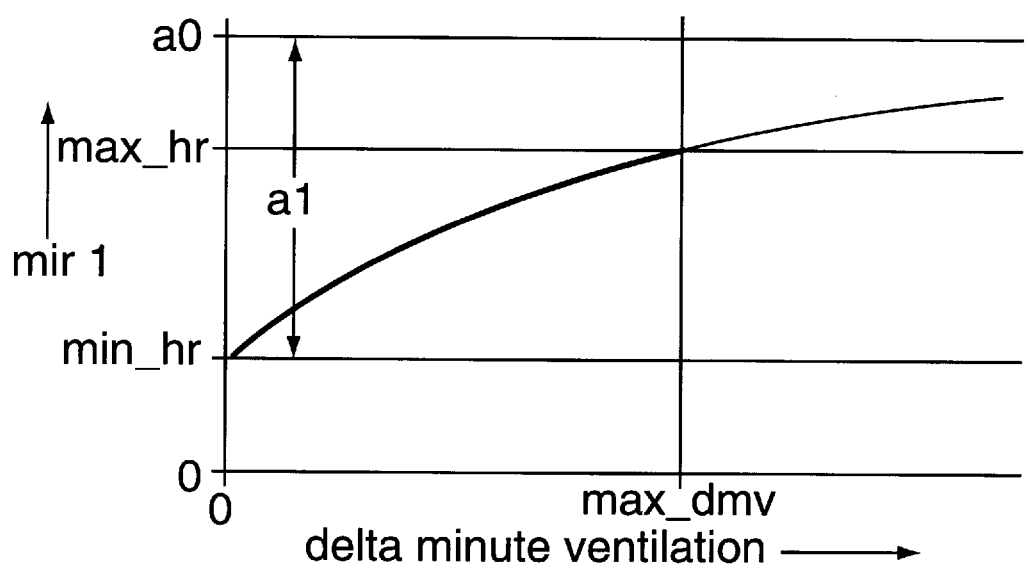
FIG. 10 shows an exponential mapping function mapping dmv into MIR.

More particularly, it has been found that an excellent fit can be generated if an exponential mapping function is used. One such function is shown in FIG. 10. To save computational time, the exponential function may be performed by an interpolated table look-up function. The logarithmic function used to compute max_dmv is evaluated only by the programmer, at the time min_hr or max_hr is changed. The rate response factor (RRF) is defined so that one unit change in RRF relates to a 10% change in the peak value minute ventilation signal. It may be computed and displayed by the programmer, or may be entered by the user and used to initialize mv_gain.

The mapping function of FIG. 10 is defined by the following:

MIR1=a0–a1 * exp (–dmv/a2)

a0=230 pulses per minute (a0 is the upper heart rate asymptote)

a1=a0–min_hr (a1 determines min_hr)

a2=133 pulses per minute (a2 determines the hr/mv slope)

dmv=filtered delta minute ventilation from delta mv generator 102 max_dmv=the maximum value of DMV which is mapped to max_hr max_hr=the programmed maximum value of paced heart rate RRF=rrf_const+In (mv_gain/max_dmv)/1n (1.1)

mv_gain=max_dmv * 1.1(RRF-rrf_const)

rrf_const is chosen to establish the nominal RRF value.

Returning to FIG. 5, the parameter MIR is then used to generate a metabolic indicated rate interval (MRI) by calculator 106. The paced pulse interval is inversely related to the paced heart rate as indicated by the following equation.

ppi=60000/phr ppi=paced pulse interval, milliseconds phr=paced heart rate, pulses per second Other time intervals of the pacing cycle are computed by the state machine 53C (FIG. 4) using the paced pulse interval and/or the heart rate.

Although the invention has been described with reference to several particular embodiments, it is to be understood that these embodiments are merely illustrative of the application of the principles of the invention. Accordingly, the embodiments described in particular should be considered exemplary, not limiting, with respect to the following claims.

We claim:

1. A rate responsive pacemaker comprising:
   a sensor for sensing cardiac activity and generating a corresponding cardiac sense signal;
   a pace generator for generating pacing signals in response to a first and a second command signal;
   a metabolic demand sensor for sensing a metabolic demand parameter and generating a corresponding metabolic indicated signal;
   a noise sensor for generating a noise signal when sensing noise; and
   a controller receiving said sensor, metabolic indicated and noise signals and generating said first command responsive to said metabolic indicated signal in absence of noise and said second command independent of said metabolic indicated signal in the presence of noise.

2. The pacemaker of claim 1 wherein said controller includes a mode selector, said mode selector receiving said sensor signal and generating a first mode signal when said sensor signal indicates an intrinsic cardiac rate below a preset value and a second mode signal when said intrinsic cardiac rate is above said preset value.

3. The pacemaker of claim 1 wherein said metabolic demand parameter comprises a thoracic impedance.

4. The pacemaker of claim 1 wherein said controller further receives signals indicative of the lead impedance and wherein said controller generates said second command if said impedance exceeds a preset threshold.

5. The pacemaker of claim 4 wherein said controller generates a third command in response to a high impedance, said third command being sent to said metabolic demand sensor to disable the same.

6. A rate response pacemaker comprising:
   a lead extending to a cardiac chamber;
   a sensor for sensing cardiac activity from said lead and generating a corresponding cardiac sense signal;
   a pace generator for generating pacing signals in response to a first and a second command signal;
   a metabolic demand sensor for sensing a metabolic demand parameter and generating a corresponding metabolic indicated signal;
   a noise sensor for generating a noise signal when sensing noise on said lead; and
   a controller receiving said sensor, metabolic indicated and noise signals and generating said first command responsive to said metabolic indicated signal in absence of noise and said second command independent of said metabolic indicated signal in the presence of noise.

7. The pacemaker of claim 6 wherein in the presence of noise said controller generates commands for pacing at a rate prior to noise detection.

8. The pacemaker of claim 6 further comprising a test generator for generating a test pulse and a response sensor for sensing a response on said lead to said test pulse.

9. The pacemaker of claim 8 wherein said response generator senses said response to determinate said metabolic demand parameter.

10. The pacemaker of claim 9 wherein said test pulse measures a transthoracic impedance.

11. The pacemaker of claim 8 wherein said test generator generates a first test pulse and a second test pulse and wherein said noise is detected by comparing responses from said lead to said first and second test pulses.

12. The pacemaker of claim 8 wherein said test generator generates multiphase test signals.

13. A pacemaker comprising:

a sensor for sensing intrinsic activity in a patient's heart and generating in response sensed signals;

a pace generator for generating pacing pulses in response to commands;

a controller receiving said sensed signals and generating in response said commands; and a noise sensor sensing external noise and in response altering the operation of said controller, said noise sensor including a test generator for generating two test pulses of equal magnitude and a test sensor for comparing the responses to said test pulses, said response being indicative of said external noise.

14. A pacemaker comprising:

a sensor for sensing intrinsic activity in a patient's heart and generating in response sensed signals;

a pace generator for generating pacing pulses in response to commands;

a controller receiving said sensed signals and generating in response said commands; and a noise sensor sensing external noise and in response altering the operation of said controller, said noise sensor including a test generator for generating a multiphase test pulse, said multiphase test pulse including at least two test portions of equal magnitude but different phases.

* * * * *